United States Patent [19]

Dragan

[11] Patent Number: 5,676,543
[45] Date of Patent: Oct. 14, 1997

[54] GUM TISSUE RETRACTION DEVICE AND METHOD

[75] Inventor: William B. Dragan, Easton, Conn.

[73] Assignee: Centrix, Inc., Shelton, Conn.

[21] Appl. No.: 400,849

[22] Filed: Mar. 8, 1995

[51] Int. Cl.⁶ .................................................. A61C 5/14
[52] U.S. Cl. ........................... 433/136; 433/37; 433/71; 433/214
[58] Field of Search .......................... 433/37, 71, 214, 433/136

[56] References Cited

U.S. PATENT DOCUMENTS

| | | | |
|---|---|---|---|
| 4,468,202 | 8/1984 | Cohen | 433/214 X |
| 4,543,063 | 9/1985 | Cohen | 433/215 X |
| 4,551,100 | 11/1985 | Fischer | 433/218 |
| 4,677,139 | 6/1987 | Feinmann et al. | 433/215 X |
| 4,961,706 | 10/1990 | Jefferies | 433/214 |
| 5,190,457 | 3/1993 | Schreinmakers | 433/214 |
| 5,213,498 | 5/1993 | Pelerin | 433/37 |
| 5,362,495 | 11/1994 | Lesage | 433/228.1 X |

Primary Examiner—Nicholas D. Lucchesi
Attorney, Agent, or Firm—Fattibene and Fattibene; Paul A. Fattibene; Arthur T. Fattibene

[57] ABSTRACT

A moldable material formed over teeth with a second flowable material containing an astringent placed into the impression of the teeth in the moldable material providing retraction and hemostasis at the gum line. A moldable material, preferably a silicone, may contain an astringent such as aluminum ammonium sulfate is made into a mold of teeth. The impression formed in the mold of the teeth is filled with a less viscous or initially flowable material also containing an astringent. The mold with the flowable material is placed over the teeth. The initially flowable material preferably sets into a solid. The flowable material may be made of a condensation silicone having a base and catalyst. The mold helps to apply pressure to the flowable material which is transmitted to the gum tissue resulting in retraction and hemostasis.

21 Claims, 1 Drawing Sheet

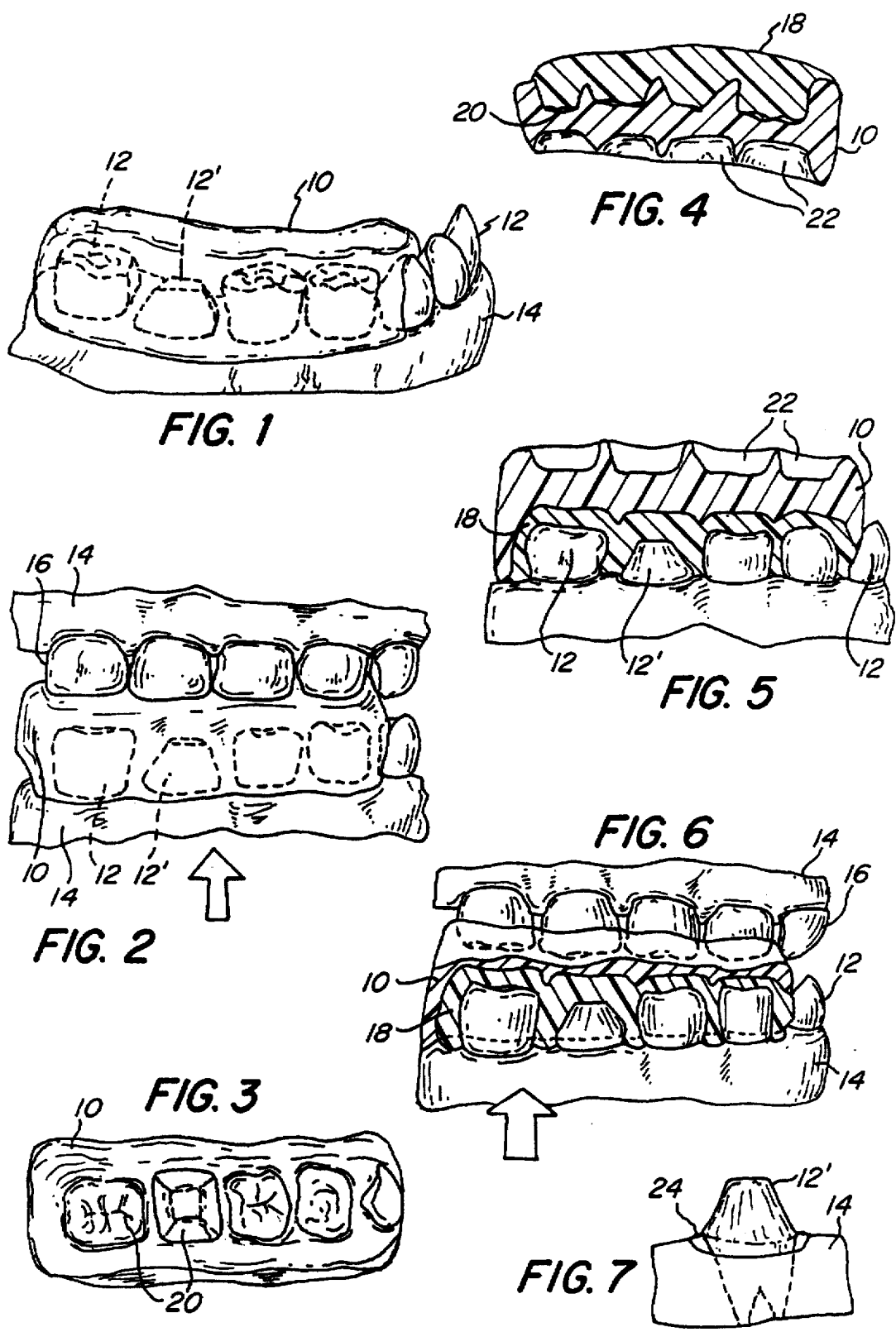

GUM TISSUE RETRACTION DEVICE AND METHOD

FIELD OF INVENTION

This invention relates in general to retraction of gum tissue as required in various dental procedures, and more particularly to the application of an astringent and/or hemostatic agent to gum tissue surrounding a tooth in preparation for taking an impression as required for making dental crowns and bridges or the like.

BACKGROUND OF THE INVENTION

In many dental procedures, such as crown and bridge procedures, it is necessary to take an impression of a patient's tooth or teeth. In order to take a good impression it is necessary to retract the gum from around the patient's tooth or teeth and stop any minor bleeding. This is most commonly done by packing the area between the gum or gingiva and a tooth with retraction cord or string. The retraction cord is usually impregnated with an astringent, such as aluminum chloride, aluminum potassium sulfate, epinephrine or the like, and forced or packed between the tooth and gum or gingiva. The use the retraction cord both chemically and mechanically stops the gingiva from oozing fluid or blood, and creates a desired dry space between the tooth and the surrounding gum tissue. As a result a good impression can be made that will capture all the margins for a crown or bridge preparation. The packing of retraction cord by the dentist is inherently both time consuming and tedious. Additionally, it is extremely uncomfortable for the patient.

Methods have been developed in an effort to obviate the disadvantages of the foregoing described retraction cord packing procedure. One such method uses a compression cap, which is a device in the form of a soft cup which is placed over the tooth after a retraction cord has been positioned about the base of the tooth. The patient then bites onto the compression cap to force the string between the gum tissue or gingiva and the tooth. Still another method requires the use of a hydrocolloid material which is injected about the tooth to effect the retraction. However, hydrocolloid material exerts no pressure to aid retraction and hemostasis. Additionally, the hydrocolloid material requires other equipment including a boiler and conditioner to heat the hydrocolloid material to achieve the proper consistency required to effect the desired retraction. Such equipment is costly and requires counter space and storage facilities which are generally at a premium in a dental operation. Also, the hydrocolloid materials, being basically comprised of water, do not create any pressure which greatly facilitates hemostasis and retraction. Hemostasis and retraction are essential to the taking of a good impression.

Therefore, there is a need for developing improvements to the practice of retracting the gingiva as required in many dental procedures that is easy for the dentist to perform and more comfortable for the patient. As a result the patient will be provided with better dentistry at a lower cost.

SUMMARY OF THE INVENTION

The present invention relates to a device in the form of a tooth cast or mold made by utilizing a heavy body putty type moldable material suitable for impressions, such as a silicone, which can be readily applied to a given tooth or teeth and surrounding area to form the mold. The moldable material may include as a component part thereof a suitable styptic substance or astringent. The moldable material may be of a type that sets into a solid.

After the mold has been formed about the tooth and gum area, it is removed and a less viscous flowable material incorporating a styptic substance or astringent is then placed in the impression of the tooth and gum area formed in the mold. The mold, together with the less viscous material, is then returned to the tooth and gum area, whereupon placement on the patient causes the less viscous material to flow and to be forced between the tooth and the gum creating both hemostasis and retraction of the gum tissue. The less viscous material may be of such a nature that it initially flows between the tooth and gum, and then sets into a solid. When the less viscous material sets, it forces a sulcus or track to be formed about the tooth. The compression of the less viscous material, containing an astringent, by the mold thus creates the necessary pressure and chemical action to cause hemostasis or stopping the flow of blood, and simultaneously effects the desired retraction of the gingiva. Upon the removal of the mold the dentist is immediately able to make a good impression of the tooth and gum area as required in making dental crowns and bridges or the like.

Accordingly, it is an object of the present invention to provide a product or device and a method for effecting gum retraction and hemostasis simply and expediently.

It is another object of the present invention to prepare an area for the taking of an accurate and positive impression that is void free without resorting to the tedious and time consuming use of retraction string or cord, either impregnated with chemicals or not.

It is an advantage of the present invention that it utilizes both pressure and an astringent to effect retraction and hemostasis.

It is a feature of the present invention that a mold is used together with a flowable material containing an astringent.

It is another feature of the present invention to provide a two-step method utilizing a heavy body moldable material which may or may not have a suitable styptic substance or astringent to form a mold of the tooth and its surrounding area, and utilizing the mold for compressing a less viscous material embodying an astringent to create pressure and chemical action to effect retraction of the gum tissue with a minimum or absence of bleeding.

Other objects, advantages, and features and will become more readily apparent in view of the following drawings and detail description

BRIEF DESCRIPTION OF THE DRAWINGS

FIG. 1 is a perspective view illustrating the application of the heavy body moldable material placed about the tooth in preparation of making the mold.

FIG. 2 is a view illustrating a patient biting onto the moldable coating material to form the mold.

FIG. 3 is a plan view looking into the mold after being removed from the patient.

FIG. 4 is a cross sectional view of the mold of FIG. 3 filled with a flowable material.

FIG. 5 is a partial cross section view in which the mold of FIG. 4 with the flowable material is returned to the patient's mouth.

FIG. 6 is a partial cross section view illustrating the patient biting down onto the mold as the flowable material is positioned to effect the desired retraction and hemostasis.

FIG. 7 is a view of the gum retracted from the tooth.

DETAIL DESCRIPTION OF THE PREFERRED EMBODIMENTS

Referring to the drawings, there is shown a dental device and method for practicing this invention after the tooth or teeth have been prepared for a crown, bridge, or other prosthetic reason. The present invention is used and practiced to prepare the patient's teeth for the taking of an impression used for preparation of a crown or bridge. FIG. 1 illustrates the material 10 for making the mold of a tooth or teeth 12. Tooth 12' is a prepared tooth. Only the lower quadrant is illustrated. The mold material 10 may be any moldable material such as a putty or heavy body silicone material. The silicone material may comprise a two-part system that includes a base portion and a catalyst portion which, when mixed, will quickly set or become solid. The time of setting can be varied within a desired range by controlling the respective proportion of the base and catalyst. Such silicone materials are known and are available from various manufacturers, for example Conquest by Pentron, EXAFLEX by G.C., EXTRUDE by Kerr Corporation, IMPRESS and EXPRESS by 3M, and others. While the silicone material is preferred, other materials such as polyethers, polysulfides, or any other moldable material may be used. A condensation silicone is preferred over an addition silicone because the set time of the condensation silicone can be adjusted easily with a liquid catalyst by the Dentist, and the condensation silicone will not be affected by rubber gloves. The condensation silicones are also less expensive. The addition silicone may be contaminated by rubber gloves and therefore will not set. After mixing, the mold material 10 is placed around the teeth 12 and 12', and gum 14.

In accordance with one embodiment of the present invention, the heavy body silicone material may be fortified with between five percent to twenty-five percent by weight of a suitable astringent to aid in gum tissue retraction and hemostasis. As little as one half of one percent will have some therapeutic effect, but the preferred amount is between five percent to twenty-five percent by weight. Any known astringent and/or hemostasis agent that causes retraction such as aluminum potassium sulfate or potassium aluminum sulfate, aluminum sulfate or alum, ferric sulfate, aluminum ammnonium sulfate, ferric chloride, aluminum chloride, sodium chloride, epinephrine, negatol, tannic acid, zinc chloride, zinc phenol sulfonate, or other known astringents and/or hemostatic agents may be mixed with the heavy body silicone material. Negatol is a condensation product of meta cresol sulfonic acid and formaldehyde. As much as fifty percent by weight of aluminum sulfate or alum has been used with no detrimental affect on the properties of the silicone. Additionally, the aluminum sulfate acts as a filler. Any chemical substance may be used as long as the substance aids in causing retraction of the gum tissue or gingiva.

FIG. 2 illustrates the mold material 10 placed about the lower teeth 12, 12' and gum 14 and allowed to set as the patient bites down slightly with upper teeth 16 leaving a one to two millimeter opening in the front. This is held for a minimum of one minute or until the mold material 10 sets. Another method may be to use a standard impression tray. The tray with the mold material therein is placed over the teeth and held for a minimum of one minute, or until the mold material sets. When the mold material 10 has set it is removed from the mouth, washed of debris and dried. A mold of the lower teeth 12 and 12' is thereby formed.

FIG. 3 illustrates the set mold material 10 removed from the patient's mouth. An impression 20 of the lower teeth 12 and 12' is formed in the mold material 10. The impression 20 closely conforms to the shape of the teeth 12, 12' and gum 14. The opposite side of the mold material 10, not shown in FIG. 3, will also contain a partial impression of each of the upper teeth 16.

FIG. 4 illustrates the impression 20 of the lower teeth 12 and 12' of the mold material 10 filled with a layer of flowable, syringeable or less viscous material 18 which has the proper astringent and/or hemostatic agent for causing retraction. The partial impression 22 of the upper teeth 16 can be seen in FIG. 4. The flowable material 18 is formed with between five percent and twenty-five percent by weight of an astringent and/or hemostatic agent similar to that hereinbefore described. As indicated before, as little as one half of one percent may have a therapeutic effect. Additionally, as much as fifty percent by weight of aluminum ammonium sulfate has been incorporated into a light body condensation silicone without any effect on the set of the material. The flowable material needs only to be initially flowable and may set into a solid after flowing near or between the tooth and gum. However, preferably the initially flowable material will set. The flowable material therefore, may be any of the silicone materials described above in relation to the mold material, or some other material that is compatible with the mold material. Preferably the initially flowable material may be a vinyl polysiloxane.

FIG. 5 illustrates the mold material 10 with the flowable material 18 returned to the patient's mouth over lower teeth 12 and 12'. The flowable material 18 begins to flow around the teeth 12, 12' and gum 14. The flowable material 18 needs only be firm enough for easy placement, and thin enough to flow around the teeth 12, 12' and gum 14 when a slight pressure is applied.

FIG. 6 illustrates the patient exerting a slight pressure on the mold material 10 assuring that the flowable material 18 is forced between the teeth 12, 12' and gum 14. The mold material 10, acting like a dam, causes the flowable material 18 to exert pressure along the gingival line forming a sulcus, groove, or trough. The pressure along with the astringent creates both hemostasis and retraction of the gum tissue 14. In one embodiment the flowable material will set facilitating hemostasis and retraction as well as ease of removal. After a predetermined period of time sufficient for the initially flowable material 18 to set, preferably approximately five minutes, the entire moldable material 10 with the set initially flowable material 18 is removed. Upon removal, the dentist can then proceed to take an impression of teeth 12 and 12' using standard materials and known impression techniques.

FIG. 7 illustrates the sulcus 24 formed around the prepared tooth 12' according to the present invention.

The method utilizing the present invention can be described as follows. The tooth is conventionally prepared for a bridge or crown. After preparation of the tooth 12' a first mold material is prepared using a silicone material and a catalyst. The first mold material may be mixed on a glass slab with the first mold material cross hatched prior to adding the liquid catalyst to ensure proper coverage of the catalyst. The mold material is mixed for a short time depending on the amount of catalyst used. The first mold material is placed either in a disposable plastic tray or formed in an elongated cylinder and placed about the patient's teeth by hand. After the first mold material has set, approximately one to two minutes, the first mold material is removed, washed, and dried. A second initially flowable material containing an astringent and/or hemostatic agent is mixed with a catalyst and placed in the impressions of the teeth formed in the set first mold material. The first set mold material and the second initially flowable material are placed over the teeth, in the disposable tray if used, and the patient instructed to bite down or hold the tray. After about five minutes the initially flowable material should be set and the retraction complete. The set mold material and the now set initially flowable material is removed and discarded. The gum surrounding the prepared teeth is now retracted and ready for taking of an impression for the making of the bridge or crown using standard techniques.

It will be understood that the moldable material 10 used to make the original mold need not include any astringent component, as it is the second flowable or less viscous material 18 which is the primary source of the astringent to the teeth 12, 12' and gum 14. The incorporation of the astringent in the mold material 10 is not as critical as the need of the astringent in the flowable or less viscous material 18. However, incorporating an astringent in the moldable material 10 will function as an additional aid in providing retraction and hemostasis. If desired, the moldable material 10 may be formed of a suitable color which may be different from that of the flowable material 18 so as to distinguish the two different materials. For example the moldable material 10 may be blue and the initially flowable material may be purple.

The retraction device and method herein described is relatively simple and expedient and results in a positive retraction of the gum tissue so as to insure that all margins can be captured by the subsequent impression procedure. The invention described further reduces the trauma and discomfort experienced by the patient relative to prior retraction procedures.

The present invention provides enhanced results with much greater ease for the dentist. Additionally, the present invention provides much greater comfort for the patient. Accordingly the present invention greatly advances the art of dentistry.

While the present invention has been described with respect to various embodiments, various modifications may be made without departing from the spirit or scope of this invention.

What is claimed is:

1. A tissue retraction device for use in dentistry to create a space between a tooth and the gum tissue preliminary to the taking of an impression comprising:

a cast forming a negative impression of the tooth and its surrounding area, said cast being formed of a moldable casting material, and a layer of a settable syringeable material disposed in the negative impression of said cast, said layer of syringeable material containing an astringent, whereby said cast forms a dam for causing said syringeable material to exert a pressure at the gingival line of the gum.

2. A tissue retraction device for use in dentistry to create a space between a tooth and the gum tissue preliminary to the taking of an impression comprising:

a cast forming a negative impression of the tooth and its surrounding area, said cast being formed of a moldable casting material, and a layer of a settable syringeable material disposed in the negative impression of said cast, said layer of syringeable material including approximately 0.5% to 50% by weight of an astringent material, whereby said cast forms a dam for causing said syringeable material to exert a pressure at the gingival line of the gum.

3. A tissue retraction device as defined in claim 2 wherein the astringent is selected from a group consisting of at least one of aluminum potassium sulfate, aluminum sulfate, ferric sulfate, aluminum ammonium sulfate, ferric chloride, aluminum chloride, sodium chloride, epinephrine, negatol, tannic acid, zinc chloride, zinc phenol sulfonate.

4. A tissue retraction device as defined in claim 1 wherein:

said layer of syringeable material includes approximately 5% to 25% by weight of an astringent material.

5. Method of effecting tissue retraction comprising the steps of:

forming a mold having a negative impression of a tooth and surrounding area being prepared for the taking of an impression, removing the mold so formed from the tooth, filling the negative impression with a layer of syringeable coating material containing an astringent, placing the mold and layer of syringeable coating material onto the tooth being prepared for the impression, exerting a pressure on said mold and layer of syringeable material as said syringeable material is allowed to set under pressure whereby the astringent and applied pressure stops any bleeding and retracts the tissue about the tooth.

6. The method as defined in claim 5 and including the step of utilizing a heavy body, putty type silicone material to form said mold.

7. The method as defined in claim 6 and including the step of incorporating in said silicone material an astringent.

8. The method as defined in claim 5 wherein the astringent incorporated in said syringeable layer is selected from the group consisting of at least one of aluminum potassium sulfate, aluminum sulfate, ferric sulfate, aluminum ammonium sulfate, ferric chloride, aluminum chloride, sodium chloride, epinephrine, negatol, tannic acid, zinc chloride, zinc phenol sulfonate.

9. The method as defined in claim 8 and including the step of:

incorporating approximately 0.5% to 50% by weight of said astringent in said syringeable layer.

10. The method as defined in claim 5 and including the step of forming said syringeable layer of a silicone material having a viscosity less than that of the mold material.

11. A dental kit comprising:

a moldable material capable of being formed and holding its shape; and a flowable material containing an astringent causing retraction of gum tissue.

12. A dental kit as in claim 11 wherein:

said moldable material contains a substance causing retraction of gum tissue.

13. A dental kit as in claim 11 wherein:

said flowable material is only initially flowable and subsequently sets into a solid.

14. A dental kit as in claim 13 wherein:

said flowable material is silicone.

15. A dental kit as in claim 14 wherein:

the silicone is a two part silicone having a base and a catalyst.

16. A dental kit as in claim 15 wherein:

the silicone is a condensation silicone.

17. A dental kit as in claim 11 wherein:

said moldable material is one color; and said flowable material is another color.

18. A method of retracting gingiva or gum tissue comprising the steps of:

forming a mold of a patient's tooth and gum;

removing the mold;

placing within the mold a flowable material containing a substance causing retraction; and replacing the mold on the patient's tooth and gum.

19. A gum tissue or gingiva retraction devise used in preparation for taking an impression necessary for preparing a bridge or crown for a patient comprising:

a first silicone material;

a first catalyst, said first catalyst causing said first silicone material to set after a predetermined period of time when mixed with said first silicone material, said first silicone material and said first catalyst forming a mold of at least one of the patient's teeth after setting;

a second silicone material, said second silicone material being initially flowable and initially less viscous than said first silicone material and containing a chemical substance causing retraction of the gum tissue or gingiva when placed in contact with the gum tissue or gingiva;

a second catalyst, said second catalyst causing said second silicone material to set after a predetermined period of time when mixed with said second silicone material, said second silicone material and said second catalyst being placed within the mold after mixing, whereby the mold containing the second silicone material mixed with said second catalyst is placed within the patient's mouth before said second silicone material has set and said second flowable silicone material is in a flowable state so that said second silicone material flows around the patient's teeth and gum tissue causing retraction of the patient's gum tissue and a sulcus to be formed.

20. A gum tissue retraction dental kit comprising:

a moldable material capable of forming an impression of a tooth and holding its shape; and a flowable material, said flowable material containing approximately 0.5% to 50% by weight of an astringent agent.

21. A gum tissue retraction dental kit comprising:

a moldable material capable of forming an impression of a tooth and holding its shape; and a flowable material, said flowable material containing approximately 0.5% to 50% by weight of a hemostatic agent.

* * * * *